US006291201B1

(12) United States Patent
Garman

(10) Patent No.: US 6,291,201 B1
(45) Date of Patent: *Sep. 18, 2001

(54) FLUORESCENCE ENERGY TRANSFER SUBSTRATES

(75) Inventor: Andrew John Garman, Chester (GB)

(73) Assignee: Zeneca Limited, London (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/557,005

(22) PCT Filed: May 27, 1994

(86) PCT No.: PCT/GB94/01153

§ 371 Date: Nov. 17, 1995

§ 102(e) Date: Nov. 17, 1995

(87) PCT Pub. No.: WO94/28166

PCT Pub. Date: Dec. 8, 1994

(30) Foreign Application Priority Data

May 27, 1993 (GB) .................................................. 9310978

(51) Int. Cl.[7] .............................. C12Q 1/37; C12N 9/48; C12N 9/50; G01N 33/52
(52) U.S. Cl. .............................. 435/23; 435/24; 435/212; 435/219; 435/968; 530/300; 530/333; 530/334; 530/402
(58) Field of Search .................................... 435/212, 219, 435/23, 968, 24; 530/333, 402, 334, 300

(56) References Cited

U.S. PATENT DOCUMENTS

| 5,011,910 | 4/1991 | Marshall et al. | 530/329 |
| 5,173,434 | * 12/1992 | Morris et al. | 436/172 |

FOREIGN PATENT DOCUMENTS

| 428000 | * 5/1991 | (EP) . |
| WO 91/09310 | 6/1991 | (WO) . |
| 91 16336 | 10/1991 | (WO) . |
| 92 00388 | 1/1992 | (WO) . |

OTHER PUBLICATIONS

Haugland, Handbook of Fluorescent Probes and Research Chemicals, 6th edition, 1992 (Molecular Probes: Eugene, OR) pp. 10, 11, 92 and 93.*

Geoghegan et al. "Site–directed conjugation of nonpeptide group to pepetides and proteins via periodate oxidation of a 2–amino alcohol. Application of modification at N–terminal serine" (1992) bioconjugate Chem., 3, pp. 138–146.*

Haugland, Handbook of Fluorescent Probes and Chemical, 6th edition, 1996 (Molecular Probes: Eugene, OR) p. 48.*

Maggiora, et al: "A General Method for the Preparation of Internally Quenched Fluorogenic Protease Substrates Using Solid–Phase Peptide Synthesis", J. Med.Chem., vol. 35, No. 21, 1992, pp. 3727–3730, see the whole document.

Geoghegan, et al: "Site–Directed Double Fluorescent Tagging of Human Renin and Collegenase (MMP–1 Substrate Peptides Using the Periodate Oxidation of N–Terminal Serine. An Apparently General Strategy for Provision of Energy–Transfer Substrates for Proteases", Bioconjugate Chem., vol. 4, No. 6, 1993, pp. 537–544, see the whole document.

Carmel, et al: "Use of sbstrates with fluorescent donor and acceptor chromophores for the kinetic assay of hydrolases", FEBS Letters, vol. 30, No. 1, 1973, pp. 11–14, see pp. 11–13.

Wang, et al: "Design and synthesis of new fluorogenic HIV protease substrates based on resonance energy transfer", Tetrahedron Letters, vol. 31, No. 45, 1990, pp. 6493–6496, see the whole document.

Ashcom et al, "Self–Quenched Fluorogenic Protein Substrates for the Detection of Cathepsin D and Other Protease Activities," Analytical Biochemistry 176,261–264 (1989).

Garcia–Echeverria et al, "New intramolecularly quenched fluorogenic peptide substrates for the study of the kinetic specificity of papain," vol. 297, Feb. 1992, No. 1, 2, 100–102.

Pennington et al, "Synthesis of a Fluorogenic Interleukin–1β Converting Enzyme Substrate Based on Resonance Energy Transfer," Peptide Research, vol. 7, No. 2 (1994) pp. 72–76.

Geoghegan et al, "Site–Directed Conjugation of Nonpeptide grouops to Peptides and Proteins via Periodate Oxidation of a 2–Amino Alcohol, application to Modification at N–Terminal Serine," Bioconjugate Chem., vol. 3, No. 2, 1992 pp. 138–146.

Matayoshi et al, "Novel Fluorogenic Substrates for Assaying Retroviral Proteases by Resonance Energy Transfer," Science, vol. 247, Feb. 23, 1990, pp. 954–958.

(List continued on next page.)

Primary Examiner—Jon P. Weber
(74) Attorney, Agent, or Firm—Pillsbury Winthrop LLP

(57) ABSTRACT

A method for the preparation of a fluorescence resonance energy transfer (FRET) substrate having donor and acceptor species on opposite sides of a proteolytic cleavage site and wherein the donor and/or acceptor species are attached via the side chain(s) of amino acid(s) therein. The method comprises contacting a reactive donor or acceptor species with a polypeptide substrate having the side chain(s) of amino acid(s) therein adapted for reaction with the reactive species and then contacting the substrate so obtained with a corresponding reactive donor or acceptor species. Novel FRET substrates so prepared and their use in assays to identify modulators of protease activity.

18 Claims, 2 Drawing Sheets

OTHER PUBLICATIONS

Miki et al, "Kinetics of Structural Changes of Reconstituted Skeletal Muscle Thin Filaments Observed by Fluorescence Resonance Energy Transfer," J. Biological Chemistry, vol. 268, No. 10, Apr. 5, 1993, pp. 7101–7106.

Wang et al, "Fluorogenic Peptides Containing Only α–Amino Acids," Biochemical and Biophysical Research Communications, vol. 201, No. 2, Jun. 15, 1994, pp. 835–840.

Dobryszycki et al. "Fluorescence resonance energy transfer studies on the proximity between lysine–107 and cysteine–239 in rabbit muscle aldolase," Biochim. Biophys. Acta (1988) 956: 217–223.*

Tolan et al. "The complete nucleotide sequence for rabbit muscle Aldolase A messenger RNA," J. Biol. Chem. (Jan. 1984) 259(2): 1127–1131.*

Carey et al. "Advanced Organic Chemistry: Part B: Reactions and Synthesis," (1984) (Plenum Press; New York), pp. 199–203.*

Latt et al., "Fluorescence Determination of Carboxypeptidase A Activity Based on Electronic Energy Transfer" (1972) Anal. Biochem., 50(1), 56–62.*

Carmel et al., "An Intramolecularly Quenched Fluorescent Tripeptide as a Fluorogenic Substrate of Angiotensin–I–Converting Enzyme and of Bacterial Dipeptidyl Carboxypeptidase" (1978) Eur. J. Biochem., 87(2), 265–273.*

Stryer, L., "Fluorescence Spectroscopy of Proteins", Science, vol. 162, pp. 526–533, Nov. 1968.*

Yaron et al., "Intramolecularly Quenched Fluorogenic Substrates for Hydrolytic Enzymes", Anal. Biochem., 95(1), pp. 228–235, May 1979.*

Boigegrain et al., "Fluorogenic Substrate Peptides for Aspartyl Proteases", C.R. Acad. Sci. Paris, vol. 310, Ser. III, No. 10, pp. 465–470, May 1990.*

Juliano et al., "A Selective Assay for Endooligopeptidase A Based on the Cleavage of Fluorogenic Substrate Structurally Related to Enkephlin", Biochem. Biophys. Res. Comm., 173(2), pp. 647–652, Dec. 1990.*

Oliveira et al., "Intramolecularly Quenched Fluorogenic Peptide Substrates for Human Renin", Anal. Biochem., 203(1), pp. 39–46, May 1992.*

Pierce Handbook and General Catalog, p. 364, 1989.*

* cited by examiner

FLUORESCENCE ENERGY TRANSFER SUBSTRATES

This application claims benefit of international application PCT/GB94/01153, filed May 27, 1994.

The concept of the fluorescence energy transfer (FRET) substrate for hydrolytic enzymes was first suggested by Carmel et al. (FEBS Lett., 30, 11–14(1973)); they described a trypsin substrate using naphthyl as the donor and anthracene as the acceptor. Since then, several protease substrates have been described using this principle. In this approach the donor fluorophore and acceptor molecules are positioned either side of the bond to be cleaved and are sufficiently close such that a large proportion of the fluorescence of the donor fluorophore is quenched by radiationless energy transfer to the acceptor. Cleavage causes a large increase in separation of the donor and acceptor which is made manifest by an increase in fluorescence. Here the acceptor moiety does not need to be a fluorophore; the key requirement is that the absorption maximum should be the same as, or close to, the emission maximum of the donor fluorophore. Optionally, the acceptor may be itself a fluorophore, in which case the enzymic reaction may be followed by the decrease in energy transfer fluorescence of the acceptor fluorophore. A variety of donors and acceptors have been employed, a common pair is an "in-sequence" trytophan as the donor and dansyl as the acceptor. Energy transfer substrates are particularly useful for proteases that have significant recognition in the native substrate of amino acids C-terminal to the cleavage site; other proteases that do not have such recognition sites are conveniently measured using peptides with fluorogenic or chromogenic leaving groups.

Present FRET substrates are limited to fluorophores that require UV excitation. This limits their use especially in compound screening methods. Furthermore the donor and/or acceptor species are attached during synthesis of the peptide substrate. This generally requires specialist reagents and know-how relating to their use. Accordingly a range of donor and acceptor species cannot be readily assessed for a given substrate.

Wang et al (Tet. Lett., 1990, 13, 6493–6496) describe a method for the preparation of fluorogenic HIV protease substrates which involves the addition of donor and acceptor species to the N- and C-termini of a peptide substrate. However, as the authors acknowledge, the procedures followed which include fluorophore attachment to the C-terminus are not straightforward. Overall this paper does not disclose a generally applicable approach.

Maggiora et al (J. Med. Chem. 1992, 35, 3727–3730) describe a method for the synthesis of FRET substrates which employ a (donor) EDANS labelled glutamic acid derivative which is introduced during peptide synthesis. The disadvantage of this approach is that, if for example for reasons of poor activity, the EDANS derivative does not give a useful substrate, then a different amino acid derivative needs to be prepared and the peptide synthesised afresh. Selecting the optimum donor is therefore not straightforward.

We have now devised a novel and advantageous method for preparing FRET protease substrates wherein, after synthesis of the polypeptide substrate, a donor or acceptor is attached via the side chain of an amino acid comprised in the polypeptide. This allows a wide range of donor and acceptor pairs, many of which are commercially available, to be attached to the peptide structure. Accordingly, desirable donor and acceptor combinations may be readily selected.

In a first aspect of the present invention we provide a method for the preparation of a polypeptide substrate for proteolytic cleavage and having a donor or acceptor species attached via a side chain of an amino acid therein which method comprises contacting an appropriate reactive donor or acceptor species with a polypeptide substrate having a side chain of an amino acid therein adapted for reaction therewith.

The above method is preferably used to prepare FRET protease substrates having appropriate donor and acceptor species on opposite sides of a proteolytic cleavage site. This is achieved either by prior or subsequent reaction of the polypeptide substrate with the corresponding reactive donor or acceptor species. By "corresponding" we mean that if a donor is attached first, then a suitable energy transfer acceptor is subsequently attached or vice versa. If desired both donor and acceptor species may be attached via the side chains of amino acids therein.

The polypeptide substrate is conveniently prepared by direct synthesis, for example as outlined in Solid Phase Peptide Synthesis, E Atherton and R C Sheppard, IRL Press, 1989. The polypeptide substrate may comprise natural or non-natural (for example D-) amino acids joined by natural or modified peptide linkages, or any combination thereof.

The sites on the polypeptide substrate for attachment of reactive donor and acceptor species are conveniently provided by amino and thiol groups. More conveniently these groups are comprised in the N-terminus and the side chain of a cysteine residue respectively. Where no appropriate group is naturally present in the sequence, this may be introduced at any convenient point, preferably by replacement of a non-critical residue. By way of example the thiol group may be introduced by replacement of a non-critical residue by cysteine. It will be clear that by "adapted for reaction" we include amino acids which are either inherently adapted for reaction or chemically modified.

Alternatively, the sites on the polypeptide substrate may be provided by introduction of chemically modified residues during peptide synthesis. By "attachment via the side chain of an amino acid" we therefore include attachment via a side chain of any amino acid, whether modified or replaced by any convenient chemical linkage. We do not exclude attachment via any convenient linkage replacing the hydrogen atom at the α-carbon of the amino acid residue.

It will be appreciated that the donor and acceptor species and their means of attachment are selected such that proteolytic cleavage of the substrate is not affected to any significant extent. In general, the N-terminus of the selected peptide is chosen to be a sufficient distance from the site of proteolytic cleavage such that its modification does not significantly affect activity. This will vary from enzyme to enzyme, however, by way of example, the N terminus is conveniently at least 3 amino acids from the cleavage site, more conveniently more than 5. Likewise the point of attachment for the donor/acceptor on the side chain is selected so as not to significantly affect activity. This will also vary according to the enzyme, but by way of example, it should be at least 3, preferably 5 amino acids away from the site for proteolytic cleavage. The total distance between attachment sites needs to be such that a useful amount of energy transfer can occur. Whilst we do not wish to be bound by theoretical considerations, this will depend on the 3 dimensional conformation adopted by the peptide in solution. The worst case can be predicted by assuming both a linear structure, and that each amino acid accounts for 3.8 angstroms. Hence for 50% energy transfer and assuming a favourable alignment of dipoles, the number of amino acids separating the donor and acceptor should be less than Ro/3.8, where Ro is the distance giving 50% transfer. For a fuller discussion, see for example J. R. Lakowicz, Principles of Fluorescence Spectroscopy, Plenum, 1983. Appropriate experiments for determining the optimum positions for attachment of the donor and acceptor species will be apparent to the scientist of ordinary skill.

Where amino and thiol chemistry is employed, the polypeptide substrate is conveniently firstly contacted with a donor or acceptor species so as to attach this via the side chain of an amino acid therein. The resulting substrate is then contacted with a corresponding donor or acceptor species so as to provide a FRET protease substrate.

Therefore in a preferred aspect of the present invention we provide a method for the preparation of a FRET protease substrate having donor and acceptor species on opposite sides of a proteolytic cleavage site which method comprises contacting a polypeptide substrate having a side chain of an amino acid therein adapted via a thiol group for reaction with an appropriate reactive donor or acceptor species and then contacting an amino group of the substrate so obtained with an appropriate reactive donor or acceptor species.

Convenient reagents for reaction at thiol groups include donor/acceptors derivatised with maleimido or haloacetyl groups. These may be reacted at typically neutral or moderately alkaline pH, conveniently in stoichiometric amounts. Purification of the peptide derivative away from excess reagent, if present may conveniently be achieved for example by gel filtration or reverse phase hplc. Other methods, for example extraction, may be devised.

Convenient reagents for reaction at amino groups include donor/acceptors derivatised with isothiocyanates, active esters, such as succinimidyl esters, of carboxylic acids or sulphonyl halides. These are generally reacted at moderately alkaline pH in an excess over the peptide. Purification may be achieved for example by gel filtration or reverse phase hplc. Other methods, for example extraction, may be devised by the person of ordinary skill.

Convenient donor and acceptor reagents for use in the methods of the invention will be apparent to the chemist of ordinary skill. Such species include those disclosed in "Molecular Probes: Handbook of Fluorescent Probes and Research Chemicals"—Richard P. Haughland—Molecular Probes Inc. If a desired reagent is not commercially available its synthesis will be evident to the above chemist of ordinary skill.

If desired only one type of group is required to achieve attachment of donor and acceptor species. By way of example only amino or thiol groups, conveniently thiol groups are required. Addition of approximately, equimolar amounts of appropriate donor and acceptor reagents provides a mixture comprising about 50% of the desired substrate.

The above methods may be applied to any convenient substrate for proteolytic cleavage. A particular substrate is big endothelin. It will be appreciated that any convenient part of a substrate sequence may be used provided that the recognition site(s) and site for proteolytic cleavage are present. As convenient example is big endothelin [16–38].

The above methods may be applied to the synthesis of substrates for any suitable protease, for example trypsin, chymotrypsin, elastase, thrombin, endothelin converting enzyme, angiotensin converting enzyme, HIV protease, matrix degrading proteases, collagenases, pro-hormone processing enzymes, pro-cytokine 1, growth factor processing enzymes and signal peptidases.

It will be understood that more than one donor and acceptor species may be provided on the FRET protease substrate although in practice more than two pairs is less convenient.

In a further aspect of the present invention we provide a FRET protease substrate when prepared by the method of the invention.

It will be clear from the above that the present invention allows a wide range of donor and acceptor pairs to be readily attached to the peptide structure, enabling the most suitable pair to be selected. Factors that may be considered in this selection include the level of activity obtained, the degree of energy transfer (which will determine the initial level of fluorescence of the substrate) and the excitation and emission wavelengths of the donor or acceptor.

A particular use of the present invention is in the provision of FRET protease substrates for compound screening, for example in pharmaceutical and agrochemical areas as well as more general research. For these procedures the absorption wavelengths of the majority of test compounds are preferably avoided.

It will be appreciated that the FRET protease subtrates of the invention may be used in a variety of homogeneous and heterogeneous assays for testing compounds individually or as mixtures.

In a further aspect of the present invention we provide a FRET protease substrate comprising a visible light fluorophore. The fluorophore is preferably attached after synthesis of the polypeptide chain of the protease substrate. The visible light fluorophore is more preferably attached via a side chain of an amino acid comprised in the polypeptide chain. Suitable visible light fluorophores (excitation maximum of the donor above about 350 nm) include fluorescein, Lucifer Yellow, acridine Orange, rhodamine and its derivatives, for example tetramethylrhodamine and Texas Red, and fluorescent chelates or cryptates of Europium. A preferred fluorophore is fluorescein.

Suitable energy transfer pairs may be found in the literature, for example in Applications of Fluorescence in Immunoassays (I. A. Hemmila, Wiley Interscience, 1991) or may be devised by a person of ordinary skill in accordance with energy transfer principles for example as outlined by J. R. Lakowicz, Principles of Fluorescence Spectroscopy, Plenum, 1983.

The method of the invention will now be illustrated but not limited by reference to the following:

1. A desired peptide sequence is selected which encompasses the site for proteolytic cleavage.
2. A position C-terminal to the site which can be mutated to cysteine and used as an attachment site without loss of substrate activity is selected.
3. The above peptide is synthesised with:
   a) a free N-terminus (the C-terminus can be free or amidated as required);
   b) any lysines C-terminal to the site for proteolytic cleavage or considered to be non-tolerant with respect to enzyme activity is either "mutated" to a non-reactive analogue (eg. arginine or dimethyl lysine) or reversibly protected;
   c) any lysines N-terminal to the site for proteolytic cleavage may be treated as above or, if they are considered to be tolerant to conjugation, can be left in place (in which case the N-terminus may be modified if desired);

The peptide now has one or more amino groups on one side of the cleavage site and a unique thiol on the other side. A wide range of thiol reactive and amino reactive derivatives of fluorophores and acceptor molecules are available commercially, including many that operate in the visible region of the spectrum. With the above peptide it is therefore possible to synthesise a range of convenient energy transfer substrates with different pairs and in different orientations.

Where big endothelin [16–38] is used as the FRET protease substrate the above complications do not apply since there are no lysines. We have evidence that for this substrate the choice of donor-acceptor pair has a significant effect on activity and that therefore the ability to screen different pairs and orientations is very useful.

Peptides containing free cysteines are unlikely to be common but we anticipate that these can be accomodated in an analogous fashion to the approach described above for lysine.

The invention will now be illustrated but not limited by reverence to the following Examples and Figures.

EXAMPLE 1

Preparation of the Starting Peptide

Figure 1:
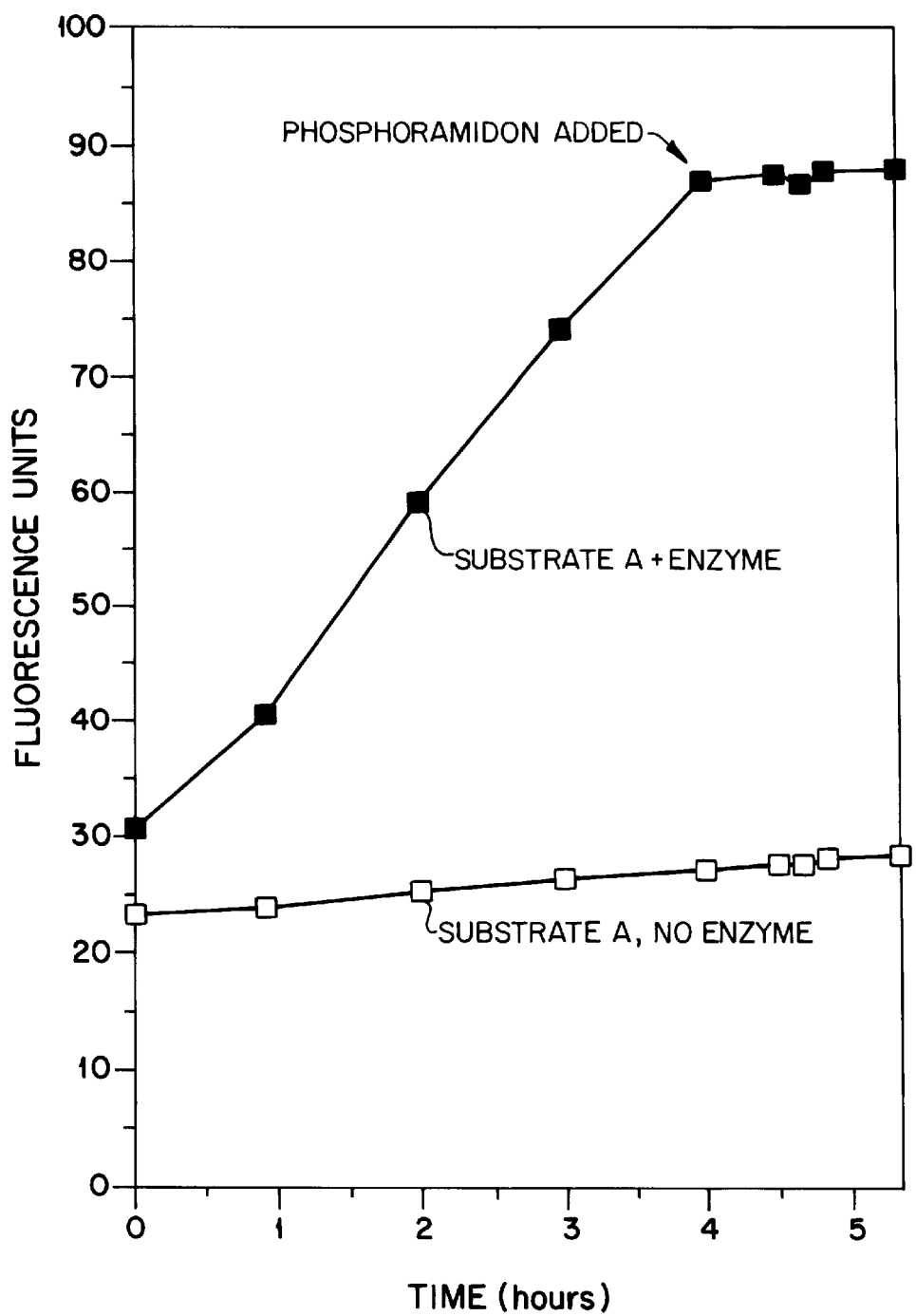
FIG. 1 illustrates the course of two reactions as measured with respect to time (x-axis) and fluorescence units (Y-axis). In the first of these only substrate A is added to the reaction mixture whereas in the second both substrate A and enzyme are added. Phosphoramidon is added to terminate this second, enzyme catalysed, reaction.

The peptide sequence selected was derived from that of human big endothelin-1, 16–37, with Glu-26 changed to Cys:
H.His.Leu.Asp.Ile.Ile.Trp.Val.Asn.Thr.Pro.Cvs.His.-Val.Val.Pro.Tyr.Gly. Leu.Gly.Ser.Pro.Arg.OH This peptide (peptide I) was synthesised on a polyamide support using conventional Fmoc chemistry, as described in Solid Phase Peptide Synthesis, E Atherton and R C Sheppard, IRL Press, 1989.
Preparation of ([Cvs-26]Fluoresceinyl) Peptide I To a solution of peptide I in water (2 mg/ml), was added an equimolar amount of 5-maleimidofluorescein (Molecular Probes, added as 5 mM solution in DMSO). After 10 minutes, 0.3 volumes of 0.1M NaHCO3, 0.9% NaCl buffer pH 8.5 added. After a further 10 minutes a sample was assayed for thiol content using Ellman's reagent. The thiol content was found to be zero indicating complete coupling.
Preparation of Tetramethyrhodaminyl ([Cvs-26] Fluoresceinyl) Peptide (Substrate A)

To ([Cys-26]fluoresceinyl) peptide I was added 20 mM tetramethylrhodamine isothiocyanate (Molecular Probes, either R or G isomer or mixture) in DMSO to a final concentration of 2 mM and the reaction incubated at room temperature overnight in the dark. The mixture was desalted on a column of gel filtration resin SEPHADEX G15 equilibrated in water. The UV/visible spectrum showed peaks of similar size at 495 nm and 553 nm indicating the prescence of aproximately equimolar amounts of both fluorescein and tetramethylrhodamine moieties in the peptide.
Preparation of Dimethoxyfluorescein ([Cys-26] Fluoresceinyl) Peptide (Substrate B)

To ([Cys-26]fluoresceinyl) peptide I (0.58 ml) was added 0.116 ml of 50 mM dimethoxyfluorescein N-hydroxysuccinimide ester (prepared according to the method described in Anal. Biochem. 108, 156–161) in DMSO. After 2 hours, 0.5 ml DMSO was added to re-dissolve some precipitated material and a further 2.0 mg of the dimethoxyfluorescein reagent in DMSO (0.15 ml) was added. After a further 2 hours, the product was isolated by passage through a column of gel filtration resin SEPHADEX G15 (ca 10 ml) equilibrated with 0.2M Tris.HCl buffer, pH 7.2:DMSO, 4:1. In addition to a fluorescein absorbance at 495 nm, the UV spectrum of the product showed absorbance at 518 nm, consistent with ca 1 mole/mole dimethoxyfluorescein.
Preparation of [Cvs-26]Eosinyl) Peptide I To a solution of peptide I in water (2 mg/ml), was added an 1.1 equivalents of 5-maleimido-eosin (Molecular Probes, added as 5 mM solution in DMSO). After 15 minutes, 0.3 volumes of 0.1M NaHCO3, 0.9% NaCl buffer pH 8.5 added. After a further 15 minutes a sample was assayed for thiol content using Ellman's reagent. Since some free thiol was detected, a further 0.16 equivalents of 5-maleimdo-eosin were added. After a further reaction period of ca 0.5 hours, the thiol content was found to be zero indicating complete coupling.
Preparation of Fluoresceinyl [Cvs-26]eosinyl) Peptide I (Substrate C)

To [Cys-26]eosinyl) peptide I was added fluorescein 5-isothiocyanate (Molecular Probes) in DMSO to a final concentration of 2.5 mg/ml and the reaction incubated at room temperature overnight in the dark. The mixture was desalted on a column of gel filtration resin SEPHADEX G15 equilibrated in 0.2M Tris.HCl buffer pH 7.2. The UV/visible spectrum showed peaks of similar size at 495 nm and 553 nm indicating the prescence of aproximately equimolar amounts of both fluorescein and tetramethylrhodamine moieties in the peptide.
Evaluation of Substrates Samples of endothelin converting enzyme (ECE) were obtained according to the method of Okada et al., Biochem. Biophys. Res. Comm., 3, 1192–1198. A more purified sample, used to evaluate substrate C, was a gift of M Abbott (Zeneca).

Substrates at ca 10 $\mu$M were incubated in 0.2M Tris.HCl buffer pH 7.2 and incubated with ECE at 37 degrees C in the wells of black microtitre plates (Labsystems). Fluorescein fluorescence was measured at various time intervals on a Labsystems Fluoroskan fluorescence plate reader, with excitation and emission filters set at 490 and 535 nm respectively. After an initial incubation of ca 0.5 hours (to allow, it is believed, a stable meniscus to form) a linear increase in fluorescence was obtained. This is illustrated for substrate A in FIG. 1. This also shows a control with no enzyme present and also the effect of adding phosphoramidon, a known inhibitor of ECE, to a final concentration of 0.3 mM.

The percentage conversion per unit time was calculated for each substrate and the results compared with the conversion of that preparation of ECE on big ET, as judged by high pressure liquid chromatography (hplc), which was found to be typically ca 25% conversion per hour. The activities of the three substrates were thereby found to be:

| | Position: N-terminus | Cys-26 | Activity (big-ET = 1) |
|---|---|---|---|
| substrate A | tetramethylrhodamine | fluorescein | 0.3–0.4 |
| substrate B | dimethoxyfluorescein | fluorescein | 0.05 |
| substrate C | fluorescein | eosin | 0.10–0.15 |

The three substrates show very different levels of activity. This indicates that the method of the invention may be readily used to investigate the activity of FRET protease substrates employing different fluorophores and acceptors.

EXAMPLE 2

Preparation of Starting Peptides

The peptide sequences selected were:

1. For endothelin converting enzyme, human big endothelin-1, with Glu-26 changed to Cys:

H.His.Leu.Asp.Ile.Ile.Trp.Val.Asn.Thr-.Pro.Cys.His.Val.Val.Pro.Tyr.Gly. Leu.Gly.Ser.Pro.Arg.OH (Peptide I)

2. For staphylococcal VB protease:

H.Arg.Asn.Ile.Thr.Glu.Gly.Glu.Ala.Arg-.Gly.Ser.Val.Cys.Leu.OH (Peptide II)

The above peptides I and II were synthesised on polyamide supports using conventional Fmoc chemistry, as described in Solid Phase Peptide Synthesis, E Atherton and R C Sheppard, IRL Press, 1989.

Preparation of [Cys-13]Fluoresceinyl Peptide II

To a solution of peptide II in water (2.5 mg/ml) was added an equimolar amount of 5-maleimido fluorescein (Molecular Probes, added as a 13.3 mM solution in DMSO). After 10 minutes at room temperature, 0.3 volumes of 0.1M NaHCO$_3$, pH 8.5 was added and the solution incubated for a further 15 minutes. A sample was assayed for thiol content using Ellman's reagents: this gave 98% loss of thiol indicating essentially complete coupling.

Preparation of Tetramethylrhodaminyl [Cvs-13] Fluoresceinyl Peptide II (Substrate D)

To [Cys-13]fluoresceinyl peptide II was added 40 mM tetramethylrhodamine isothiocyanate (Molecular Probes, isomer G) in DMSO to give a final concentration of 4.3 mM and the reaction mixture incubated at room temperature overnight in the dark. The mixture was then desalted on a column of gel filtration resin SEPHADEX G15 equilibrated in water. The UV/visible spectrum showed peaks of similar size at 495 nm and 553 nm indicating the prescence of approximately equimolar amounts of both fluorescein and tetramethylrhodamine moities in the peptide.

Evaluation of the Endothelin Converting Enzyme Substrates (Substrates A. B and C)

This was effected according to the protocol set out in Example 1.

Evaluation of the Staphylococcal V8 Protease Substrate (Substrate D)

The staphylococcal V8 protease was obtained from the Pierce Chemical Co.

To a solution of substrate D (ca 0.5 micromolar in 0.2M Tris.HCl buffer, pH 7.2, 0.6 ml) in a fluorescence cuvette was added VB protease (0.04 ml, 300 units) and the increase in fluorescence monitored in a Spex Fluoromax fluorimeter with excitation at 495 nm and emission at 515 nm, and with an OD 1.0 neutral density filter and 5 nm slit widths. The incubation was performed at ambient temperature.

Figure 2:
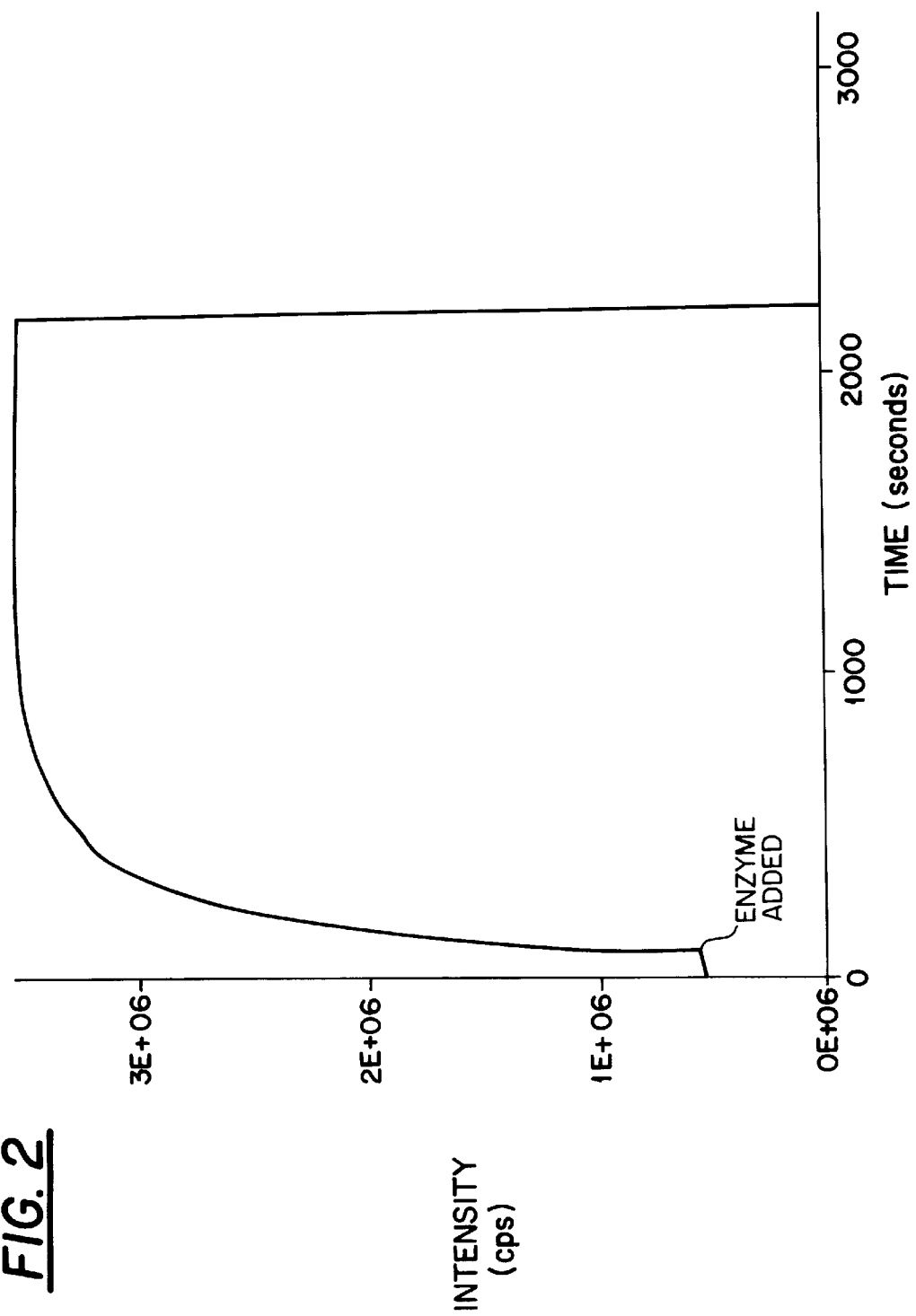
FIG. 2 shows the increase in fluorescence obtained over time using substrate D as substrate for the staphylococcal V8 protease (cf. Example 2). The reaction plateaus at a level ca 6.3 times higher than the initial level. Assuming complete conversion of substrate during the incubation, this imples that the substrate D was ca 84% quenched.

FIG. 2 shows the increase in fluorescence obtained. The reaction plateaus at a level ca 6.3 times higher than the initial level. Assuming complete conversion of substrate during the incubation, this implies that the substrate D was ca 84% quenched.

This shows that substrate D is a useful substrate for the estimation of the staphylococcal V8 protease.

What is claimed is:

1. A peptide Fluorescence Resonance Energy Transfer (FRET) substrate for identifying proteolytic cleavage within said peptide having a corresponding donor and acceptor on opposite sides of a proteolytic cleavage site of said peptide, wherein one of said corresponding donor and acceptor has been attached to said peptide by reaction between a thiol-reactive group on said one donor or acceptor and a thiol-bearing side chain on an amino acid of said peptide, wherein said amino acid bearing a thiol side chain has been introduced by replacement at a site of said peptide which does not prevent proteolytic cleavage, and wherein the other of said corresponding donor and acceptor has been attached to said peptide by reaction between an amino-reactive group on said other donor or acceptor, with an amino group of said peptide.

2. The peptide FRET substrate according to claim 1, wherein said corresponding donor and acceptor are each positioned at least 3 amino acid residues from said proteolytic cleavage site.

3. The peptide FRET substrate according to claim 1, wherein one of said corresponding donor and acceptor is a fluorophore with an excitation maximum in the visible light region.

4. A method of identifying protease activity using a peptide fluorescence resonance energy transfer (FRET) substrate comprising incubation of a sample with a peptide FRET substrate of claim 1, and detecting modulation of fluorescence following protease cleavage of said peptide FRET substrate.

5. A method of claim 4, wherein the incubation step occurs in solution.

6. A method for the preparation of a peptide Fluorescence Resonance Energy Transfer (FRET) substrate for identifying proteolytic cleavage within said peptide, comprising:

selecting a desired peptide sequence containing a proteolytic cleavage site, synthesizing said peptide with replacement of an amino acid of said peptide sequence by an amino acid bearing a thiol side chain, attaching a donor or acceptor by reaction between a thiol-reactive group on said donor or acceptor and the thiol-bearing side chain on an amino acid of said peptide, and attaching a corresponding donor or acceptor by reaction between an amino-reactive group on said corresponding donor or acceptor and an amino group of said peptide, whereby corresponding donor and acceptor are attached on opposite sides of a proteolytic cleavage site.

7. The method for the preparation of the peptide FRET substrate according to claim 6, wherein said amino group is at the N-terminus of said peptide.

8. A peptide FRET substrate prepared according to claim 6.

9. The peptide FRET substrate according to claim 1 or 8, wherein said amino group is at the N-terminus of said peptide.

10. The peptide FRET substrate according to claim 1 or 8, wherein said amino acid bearing a thiol side chain is cysteine.

11. The peptide FRET substrate according to claim 1 or 8, wherein said amino acid bearing a thiol side chain is cysteine and said amino group is at the N-terminus.

12. The peptide FRET substrate according to claim 1 or 8, wherein there is only one thiol-bearing side chain available for attachment.

13. The peptide FRET substrate according to claim 1 or 8, wherein said amino acid bearing a thiol side chain is C-terminal to said proteolytic cleavage site.

14. The method for the preparation of the peptide FRET substrate according to claim 6, wherein said reaction between a thiol-reactive group on said donor or acceptor and the thiol-bearing side chain on an amino acid of said peptide is followed by said reaction between an amino-reactive group on said corresponding donor or acceptor and an amino group of said peptide.

15. The method for the preparation of the peptide FRET substrate according to claim 6, wherein said amino acid bearing a thiol side chain is cysteine.

16. The method for the preparation of the peptide FRET substrate according to claim 6, wherein said amino acid bearing a thiol side chain is cysteine and said amino group is at the N-terminus.

17. The method for the preparation of the peptide FRET substrate according to claim 6, wherein there is only one thiol-bearing side chain available for attachment.

18. The method for the preparation of the peptide FRET substrate according to claim 6, wherein said amino acid bearing a thiol side chain is C-terminal to said proteolytic cleavage site.

* * * * *